United States Patent [19]
Bömer, deceased et al.

[11] Patent Number: 5,868,938
[45] Date of Patent: Feb. 9, 1999

[54] CHIRAL STATIONARY PHASES FOR CHROMATOGRAPHIC SEPARATION OF OPTICAL ISOMERS

[75] Inventors: Bruno Bömer, deceased, late of Bergisch Gladbach, by Karin Elfriede Bömer, neé Dick, executrix, Marcel Bömer, heir; by Guido Martin Bömer, Bonn; Rolf Grosser, Leverkusen; Walter Lange, Köln; Uwe Zweering, Düsseldorf; Burkhard Köhler, Leverkusen; Wolfram Sirges, Düsseldorf; Michael Grosse-Bley, Köln, all of Germany

[73] Assignee: Bayer Aktiengesellschaft, Leverkusen, Germany

[21] Appl. No.: 753,971

[22] Filed: Dec. 4, 1996

[30] Foreign Application Priority Data

Dec. 11, 1995 [DE] Germany ............... 195 46 136.3

[51] Int. Cl.$^6$ .................. G01N 30/02; C08F 20/54
[52] U.S. Cl. .................. 210/656; 502/402; 526/305; 526/306; 210/658; 210/198.2
[58] Field of Search ............. 526/305, 306; 210/658, 656, 198.2; 502/402

[56] References Cited

U.S. PATENT DOCUMENTS

| | | | |
|---|---|---|---|
| 4,914,159 | 4/1990 | Bomer et al. ................ | 525/328.2 |
| 4,931,525 | 6/1990 | Schwartz et al. ............. | 526/305 |
| 4,937,000 | 6/1990 | Bomer et al. ................ | 210/656 |
| 5,274,167 | 12/1993 | Lange et al. ................. | 560/40 |
| 5,354,884 | 10/1994 | Grosser et al. .............. | 560/41 |
| 5,432,251 | 7/1995 | Grosse-Bley et al. ......... | 528/246 |
| 5,432,252 | 7/1995 | Grosse-Bley et al. ......... | 528/246 |
| 5,481,026 | 1/1996 | Grosse-Bley et al. ......... | 560/153 |
| 5,510,530 | 4/1996 | Grosse-Bley et al. ......... | 564/154 |

OTHER PUBLICATIONS

B. Galli, Chirality, vol. 4, pp. 384–388 (1992).

G. Blaschke, Chromatography, Sci., vol. 40, pp. 179–198 (1988).

V.R. Meyer, Praxis der Hochleistungsflussigchromatographi, 6, (Table of Contents only), Otto Salle Verlag, Frankfurt am Main, (1989).

*Primary Examiner*—Jeffrey Smith
*Assistant Examiner*—Roberto Rabago
*Attorney, Agent, or Firm*—Sprung Kramer Schaefer & Briscoe

[57] ABSTRACT

The invention relates to chiral polymers which are bonded to a support and have improved properties, a process for the preparation of these materials and their use as chiral stationary phases in the chromatograhic separation of optical isomers, in particular of racemates into their enantiomers.

9 Claims, No Drawings

CHIRAL STATIONARY PHASES FOR CHROMATOGRAPHIC SEPARATION OF OPTICAL ISOMERS

The invention relates to chiral polymers which are bonded to a support and have improved properties, a process for the preparation of these materials and their use as chiral stationary phases in the chromatographic separation of optical isomers, in particular of ms into their enantiomers.

The separation of racemates of active compounds into their optical antipodes has gained increasing importance in recent years, since it has been demonstrated that the enantiomers of a chiral active compound often differ significantly in their actions and side-effects.

In addition to the conventional processes for separation of racemates, chromatographic splitting of racemates is becoming more and more important here. A large number of adsorbents for chromatographic splitting of racemates has already been proposed. In addition to derivatives of naturally occurring substances (often based on cellulose), synthetic polymers, such as optically active polymeric (meth) acrylamides (Blaschke et al., Chromatogr. Sci., 1988, 40, 170–198) have to date often proved to be good adsorbents in this context.

The polymeric (meth)acrylic acid derivatives of optically active amino compounds described in EP-A 379 917, for example, are also particularly suitable.

The resistance of chiral stationary phases to pressure is important for their use in practice, since high flow rates are necessary to achieve high space/time yields in the chromatographic splitting of racemates. If the resistance to pressure is not adequate, these flow rates lead to blocking of the columns.

Chiral phases which are stable to pressure are obtained when the optically active material is immobilized on an inorganic support material. Silica gels are as a rule used as inorganic support materials. The optically active polymers can be absorbed onto these silica gels, for example, by being adsorbed physically or fixed covalently. The latter can be effected by coating the silica gel surface with polymerizable groups and then carrying out copolymerization with the optically active monomers (EP 0 282 770).

Disadvantages of the processes mentioned are the often expensive preparation of the silica gel coated with polymerizable groups on the surface and, in particular, the often unsatisfactory bonding yield of the often expensive monomers on the support material. Adsorbents with a high coating of polymer also usually cannot be obtained by the processes mentioned, these being desirable in order to increase the space/time yield by higher loading during splitting of racemates.

Chiral stationary phases which can be obtained by grafting difunctional vinyl compounds, such as N,N'-diacryloyl-(1R,2R)-diaminocyclohexane, onto silica gel coated with mercapto groups (SH groups) are furthermore known (B. Galli et al., Chirality 4, 1992, 384 to 388). By using difunctional vinyl compounds, the stationary phases thus obtained are highly crosslinked and are not comparable to those based on monofunctional monomers.

With chiral stationary phases based on monofunctional vinyl compounds, it has been difficult to date to achieve high coatings of polymer with the lowest possible supply of monomer (high fixing yield). Surprisingly, it has now been found that such chiral stationary chromatography phases with a higher coating of polymer can be obtained by coating inorganic support materials with mercapto groups (SH groups) and reacting these support materials with optically active monofunctional vinyl monomers, mixtures of various optically active monofunctional vinyl monomers or mixtures of optically active monofunctional vinyl monomers with vinyl monomers which are not optically active.

According to a first aspect, the invention therefore relates to chiral stationary chromatography phases comprising an inorganic support material and chiral linear polymer groups which are based on monofunctional chiral vinyl monomers and are bonded to the support material via a sulphur atom and, if appropriate, via a spacer grouping, the polymer coating being 5 to 40% by weight based on the total weight. The polymer coating is preferably 15 to 25% by weight.

The chiral polymer groups are preferably derived from optically active (meth)acrylic acid derivatives as optically active vinyl monomers. Preferred (meth)acrylic acid derivatives are optically active (meth)acrylamide monomers of the general formula (I)

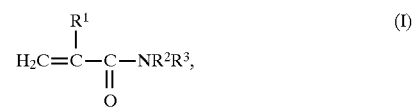

in which
[A]
$R^1$ represents hydrogen or methyl and
$R^2$ represents one of the stereoisomers of the eight particular possible stereoisomeric forms of the optically active radicals of the formulae

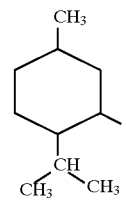

or

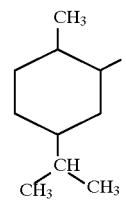

and
$R^3$ represents hydrogen,
or in which
[B]
$R^1$ has the meaning given under [A],
$R^2$ represents a radical of the formula (II)

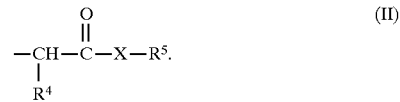

wherein
$R^4$ denotes an alkyl group having 1 to 18 C atoms or a cycloalkyl group having 3 to 8 C atoms, which are optionally substituted by hydroxyl, halogen, alkoxy or cycloalkyl having up to 8 carbon atoms, by an aryl group having up to 14 carbon atoms or by a heteroaryl group having 4 to 14 carbon atoms, which contains 1 or 2 heteroatoms from the group consisting of nitrogen, oxygen and sulphur, where the aryl or heteroaryl groups mentioned are optionally substituted by hydroxyl, halogen, alkyl or alkoxy having in each case 1 to 4 C atoms, X denotes oxygen or an $NR^6$ group, in which $R^6$ is hydrogen or represents an alkyl group having 1 to 4 C atoms, or in which $R^6$ together with $R^5$ and the nitrogen atom, forms a 5- to 7-membered heterocyclic ring, which is optionally substituted by a COO-alkyl group (1 to 4 C atoms) or by 1 or 2 alkyl groups (in each case 1 to 4 C atoms), and $R^5$ denotes a bulky hydrocarbon radical which occupies a large space and has up to 30 carbon atoms or a heteroaryl radical having 4 to 14 carbon atoms, which contains 1 heteroatom from the group consisting of nitrogen, oxygen and sulphur, where the hydrocarbon and heteroaryl radicals mentioned are optionally substituted by halogen, hydroxyl, alkyl and/or alkoxy having in each case 1 to 8 carbon atoms, with the proviso that when $R^5$ is a tertiary butyl group or X represents the radical $NR^6$, $R^1$ must be a methyl group, and $R^3$ denotes hydrogen or, together with $R^4$, denotes a tri- or tetramethylene group, or in which

[C]

$R^1$ represents fluorine, $R^2$ represents a radical of the formula (II) given under [B], wherein $R^4$ represents a straight-chain or branched $C_1$–$C_8$-alkyl, a $C_7$–$C_{12}$-aralkyl, a $C_3$–$C_{10}$-cycloalkyl, a $C_6$–$C_{14}$-aryl or a furyl, thienyl or pyridyl radical, each of which is optionally substituted by benzyloxycarbonyl, alkoxycarbonyl having up to 6 C atoms, hydroxyl, alkyl, cycloalkyl or alkoxy having in each case up to 6 C atoms, halogen, phenoxy, benzoxy, acylamino having up to 8 C atoms or by carbonylalkoxy having up to 6 C atoms, X denotes oxygen or an $NR^6$ group, in which $R^6$ represents hydrogen or straight-chain or branched $C_1$–$C_4$-alkyl or, together with $R^5$ and the nitrogen atom, forms a 5- to 7-membered ring, which is optionally substituted by an alkoxycarbonyl group having up to 6 carbon atoms or by one or two alkyl groups each having 1 to 4 carbon atoms, $R^5$ represents a straight-chain or branched $C_1$–$C_{22}$-alkyl, $C_7$–$C_{12}$aralkyl, $C_3$–$C_{10}$-cycloalkyl, $C_6$–$C_{14}$-aryl or a terpenyl radical, each of which is optionally substituted by halogen, alkyl or alkoxy having in each case 1 to 4 C atoms, and $R^3$ represents hydrogen or $C_1$–$C_4$alkyl or, together with $R^1$, forms a tri- or tetramethylene group, or in which

[D]

$R^1$ represents hydrogen, methyl or fluorine, $R^2$ represents a radical of the formula (II) given under [B], wherein $R^4$ represents a radical of the general formula (III)

—A—S(O)$_n$—R$^7$, wherein n denotes the number 0, $R^7$ represents alkyl having up to 8 C atoms, phenyl or

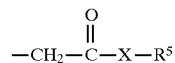

or, together with $R^3$, forms a bridge described there and

A represents a methylene or a dimethylene group, $R^5$ represents a $C_{10}$-terpenyl radical, an adamantyl radical or a decahydronaphthyl radical, or represents an alkyl radical or cycloalkyl radical having in each case up to 12 C atoms, with the exception of methyl and ethyl, which is optionally mono- or disubstituted by $C_6$–$C_{10}$-aryl, $C_1$–$C_4$-alkoxy, $C_3$–$C_{12}$-cycloalkyl or halogen, where the aryl and cycloalkyl radicals mentioned can in turn again be substituted by $C_1$–$C_4$-alkyl, X denotes oxygen or an $NR^6$ group, in which $R^6$ represents hydrogen or $C_1$–$C_4$-alkyl or, together with $R^5$, forms a nitrogen-containing 5- to 7-membered ring, which can optionally be mono- or disubstituted by $C_1$–$C_4$-alkyl or $C_1$–$C_6$-alkoxycarbonyl, and $R^3$ denotes hydrogen or methyl or, together with $R^7$, forms a methylene group, which can be mono- or disubstituted by methyl or monosubstituted by tertiary butyl, or a dimethylene group, or in which

[E]

$R^1$ represents hydrogen, methyl or fluorine, $R^2$ represents a radical of the formula (II) given under [B], wherein $R^4$ represents the radical of the formula (III) given under [D], wherein n denotes the number 1 or 2, $R^7$ represents a straigt-chain, branched or cyclic alkyl radical having up to 10 C atoms, $C_6$–$C_{14}$-aryl,

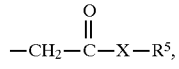

$C_2$–$C_{10}$-acyl, optionally substituted benzoyl or benzyl or, together with $R^3$, forms a bridge described there and A represents a methylene or dimethylene group which is optionally mono- or disubstituted by $C_1$–$C_4$-alkyl, $R^5$ represents a straight-chain, branched or cyclic alkyl radical having up to 20 C atoms, which is optionally mono- to trisubstituted by halogen, alkoxy having 1 to 4 C atoms, aralkoxy having 7 to 16 C atoms or aryl having 6 to 10 C atoms, X has the meaning given above under [D], and $R^3$ represents hydrogen or $C_1$–$C_4$-alkyl or, together with $R^7$, forms a methylene group or a dimethylene group, which can be mono- or disubstituted by $C_1$–$C_4$-alkyl, or in which

[F]

$R^1$ represents hydrogen, methyl or fluorine, $R^2$ represents a radical of the formula (II) given under [B], wherein $R^4$ represents $C_1$–$C_5$-alkyl, $CH_2$-O-A, $CH_2$-S-A, $(CH_2)_2$-S-$CH_3$, $CH_2$-cyclohexyl, cyclohexyl, phenyl, benzyl, 4A-O-benzyl, $CH_2$-benzyl, indolyl, $CH_2$-naphthyl or naphthyl, wherein A is hydrogen, methyl, t-butyl or benzyl, X represents —NH— and R[5] represents a radical of the general formula (IV)

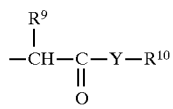

wherein
R[9] can have the meanings given for R[4] and is identical to or different from this radical,
Y represents oxygen or NR[6], wherein R[6] is hydrogen, methyl or ethyl, or, together with R[10], forms a $C_5$–$C_6$-cycloalkyl radical and
R[10] represents a straight-chain or branched $C_3$–$C_{18}$-alkyl radical or a $C_3$–$C_{12}$-cycloalkyl radical which is mono- to tetrasubstituted by $C_1$–$C_4$alkyl, or benzyl or 1-phenylethyl, or represents phenyl which is mono- or disubstituted by fluorine, chlorine, trifluoromethyl, methoxy or $C_1$–$C_4$-alkyl and
R[3] represents hydrogen.

Of these (meth)acrylamide monomers, particularly preferred compounds are those of the formula (I) according to [A], wherein
R[1] represents hydrogen or methyl and
R[2] represents one of the stereoisomers of the eight particular possible stereoisomeric forms of the optically active radicals of the formula

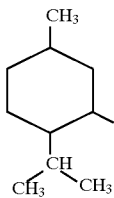

and
R[3] represents hydrogen;
or according to [B], [C], [D] and [E],
which contain the amino acid sequence of the optically active amino acids alanine, aminobutyric acid, valine, norvaline, leucine, isoleucine, terleucine, phenylglycine, naphthylglycine, phenylalanine, thienylalanine, pyridylalanine, naphthylalanine, cyclohexylglycine, cyclohexylalanine, tyrosine, tryptophan, serine, aspartic acid, glutamic acid, ornithine, lysine, proline or 6-aminopenicillanic acid
or the amino acid sequence of the optically active sulphur-containing amino acids cysteine, homocysteine, penicillamine or methionine, the SH function of which is optionally firstly alkylated, arylated, alkoxycarbonylmethylated or bonded to the amino group via an alkylene bridge, and secondly optionally oxidized to give the sulphoxide or sulphone,
or according to
[F]
which contain dipeptide units which are derived from the amino acids alanine, aminobutyric acid, valine, norvaline, leucine, isoleucine, terleucine, norleucine, neopentylglycine, serine, cysteine, methionine, hexahydrophenylalanine, hexahydrophenylglycine, phenylglycine, phenylalanine, tyrosine, homophenylalanine, tryptophan, naphthylalanine or naphthylglycine.

The preferred (meth)acrylic acid derivatives are described in EP 0 218 089, EP 0 379 917, EP 0 464 488, EP 0 520 242, EP 0 576 949 and EP 0 584 664.

In the context of this invention, the term "chiral linear polymer groups based on monofunctional chiral vinyl monomers" also includes copolymers of various monofunctional chiral vinyl monomers or of achiral and chiral vinyl monomers.

Suitable inorganic support materials carry hydroxyl or amino groups on the particle surface. Preferred support materials are silica gels. The particle size of the silica gels is between 1 and 100 μm, and particle sizes between 5 and 50 μm are preferred.

According to a further aspect, the present invention relates to a process for the preparation of the chiral stationary phases according to the invention for chromatographic separation of optical isomers by coating inorganic support materials with mercapto groups (SH groups) and subsequently reacting the resulting material with optically active monofunctional vinyl monomers, mixtures of various optically active monofunctional vinyl monomers or mixtures of optically active monofunctional vinyl monomers with vinyl monomers which are not optically active.

The possible vinyl monomers and support materials have already been described in more detail above.

The inorganic support materials modified on the surface with SH units are expediently obtained by reacting the starting material with a compound which contains at least one mercapto group. Suitable derivatizing reagents are known in principle (V. R. Meyer, Praxis der Hochleistungsflüssigchromatographie [High-performance liquid chromatography practice], Salle+Sauerländer, 6th edition 1990, p. 79 et seq. and the literature cited therein); they have the general formula Q-L-SH, wherein Q represents a reactive group which can react with the $NH_2$ or OH groups of the support material and L represents a spacer group which is inert under the appropriate conditions and ensures the necessary distance between the support material and SH group.

Silica gels are preferably coated by reaction of a non-modified silica gel with a silane of the formula $Z_1Z_2Z_3$Si-L-SH, wherein $Z_1$, $Z_2$ and $Z_3$ independently of one another represent lower alkyl, halogen, lower alkoxy or hydroxyl and L represents an optionally substituted alkylene chain having up to 7 carbon atoms.

The reaction can be carried out under base catalysis or in an acid medium. The silica gel is usually reacted in a ratio of the functionalizing reagent to the silica gel of 1:200 to 1:1, the ratio being, in particular, between 1:100 and 1:2. Silica gels which contain 0.1% to 50%, particularly preferably 0.5% to 3%, of sulphur in the form of SH groups result.

The polymerizations can be carried out in the absence of solvents or in the presence of solvents or of precipitating agents for the particular polymer. Possible free radical initiators are the agents which form free radicals and are known to the expert. Particularly preferred agents are peroxides, such as, for example, dibenzoylperoxide, dilauroylperoxide or diorthotolylperoxide, or azo compounds, such as, for example, azobisisobutyronitrile (AIBN). Mixtures of various agents which form free radicals can also be used.

After the polymerization of the optically active vinyl monomers in the presence of the support material carrying SH groups, the resulting polymer-modified materials are washed intensively with solvents for the polymer and dried.

The process described for the preparation of the chiral chromatography phases according to the invention has the advantage, compared with conventional processes, that the linking of the monomers with the support material proceeds with a high bonding yield. This is of particular advantage in the case of monomers which are expensive to prepare.

The invention furthermore relates to the use of the chiral stationary phases according to the invention for the separation of optical isomers, in particular of racemic mixtures into the optical antipodes. The composition of the mobile phase can be chosen and optimized in the customary manner, according to the nature and property of the racemate to be separated.

The ability of the materials to split racemates is expressed by the capacity ratios k'(1) and k'(2) for the enantiomers 1 and 2 and the resulting enantioselectivity value α

$$\alpha = k'(2)/k'(1)$$

The invention is illustrated by the following examples.

EXAMPLE I 300 g of silica gel (Polygosil 100, 10 μ from Macherey & Nagel) are dried at 130° C. for 3 hours under a high vacuum. The silica gel is then added to 3000 ml of dry toluene, and 9.0 g of p-toluene sulphonic acid, 2.4 ml of demineralized water and 30.0 g of 3-mercaptopropyltrimethoxysilane are added. The mixture is heated for 8 hours at reflux under nitrogen. It is then filtered with suction over a frit and the product is extracted by stirring with methylene chloride, methanol/methylene chloride (1:1) and twice more with methylene chloride, between each time being sucked thoroughly dry in each case, and finally dried for 2 hours under a high vacuum.

Elemental analysis:

C: 3.3%

H: 0.9%

N: >0.2%

S: 1.6%

EXAMPLE 1

3.0 g of the modified silica gel from Example I are initially introduced into a 100 ml three-necked flask under a nitrogen atmosphere. 1.2 g of N-methacryloyl-L-phenylalanine 1-menthylamide, 12.0 ml of dry toluene and 0.02 g of azobisisobutyronitrile are now added. The apparatus is freed from oxygen by alternately evacuating and filling with nitrogen three times and is then filled with nitrogen.

Polymerization is carried out at 60° C. for 12 hours, 0.2 g of 2,6-di-tert-butyl-4-methylphenol and 3.0 ml of bistrimethylsilylacetamide are then added and the mixture is heated at reflux for 4 hours.

Finally, it is filtered with suction over a frit (G4) and the product is extracted by stirring with methylene chloride, methanol/methylene chloride (1:1), toluene, isopropanol and again with methylene chloride and in each case filtered off with suction between each extraction. The silica gel is dried in vacuo at room temperature.

Elemental analysis gives the following results:

C: 19.5%

H: 2.7%

N: 1.6%.

EXAMPLES 2 to 4

Examples 2 to 4 were carried out in the same manner as Example 1. However, the monomer mentioned in the following table was employed.

| | | Elemental analysis | | |
|---|---|---|---|---|
| Example | Monomer | C | H | N |
| 2 | N-methacryloyl-L-leucine-1-menthylamide | 17.6 | 2.9 | 1.7 |
| 3 | N-methacryloyl-L-methionine-1-menthylamide | 16.7 | 2.7 | 1.5 |
| 4 | (+)-Camphanic acid 4-vinyl-anilide | 20.0 | 2.5 | 1.1 |

The suitability of the chiral stationary phases according to the invention may be illustrated by the following separation examples:

| Example | Racemate | α Value | $k_1'$ | Eluent (n-heptane/THF) |
|---|---|---|---|---|
| 1 | Oxazepam | 2.72 | 0.14 | 1:4 |
| | Chlormezanone | 1.45 | 0.92 | 1:1 |
| | Mandelic acid | 1.32 | 2.14 | 1:1 |
| 2 | Oxazepam | 1.85 | 0.67 | 1:4 |
| | Chlorthalidone | 1.90 | 0.93 | 1:4 |
| | Chlormezanone | 1.92 | 1.69 | 1:1 |
| 3 | Oxazepam | 2.69 | 0.73 | 1:4 |
| | Chlorthalidone | 2.43 | 0.41 | 1:4 |
| | Mandelic acid amide | 1.45 | 1.27 | 1:4 |
| 4 | N-benzoyl-2-tert-butyl-5-oxazolidone | 1.1 | 4.10 | n-heptane/isopropanol (10:1) |

The polymers bonded to the silica gels according to the invention were employed under HPLC conditions in steel columns (internal diameter: 4 mm; length: 25 cm). Elution was carried out with n-heptane/tetrahydrofuran mixtures (for example 1:1 or 1:4 v/v) at a flow rate of 1 ml/min.

We claim:

1. Chiral polymers which are bonded to a support and comprise an inorganic support material and chiral linear polymer groups which are based on monofunctional chiral vinyl monomers and are bonded to the support material via a sulphur atom and, if appropriate, via a spacer grouping, the polymer coating being 5 to 40% by weight, based on the total weight.

2. Chiral polymers bonded to a support according to claim 1, characterized in that the monofunctional chiral vinyl monomers are optically active (meth)acrylic acid derivatives.

3. Chiral polymers bonded to a support according to claim 2, characterized in that the monofunctional chiral vinyl monomers are optically active (meth)acrylamide monomers of the general formula (I)

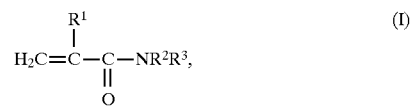

in which

[A]

$R^1$ represents hydrogen or methyl and $R^2$ represents one of the stereoisomers of the eight particular possible stereoisomeric forms of the optically active radicals of the formulae

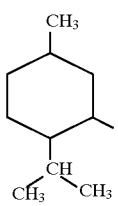

or

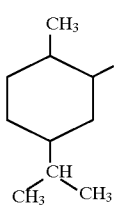

and
R³ presents hydrogen;
or in which
[B]
R¹ has the meaning given under [A],
R² represents a radical of the formula (II)

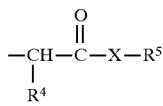 (II)

wherein
R⁴ denotes an alkyl group having 1 to 18 C atoms or a cycloalkyl group having 3 to 8 C atoms, which are optionally substituted by hydroxyl, halogen, alkoxy or cycloalkyl having up to 8 carbon atoms, by an aryl group having up to 14 carbon atoms or by a heteroaryl group having 4 to 14 carbon atoms, which contains 1 or 2 heteroatoms from the group consisting of nitrogen, oxygen and sulphur, where the aryl or heteroaryl groups mentioned are optionally substituted by hydroxyl, halogen, alkyl or alkoxy having in each case 1 to 4 C atoms,
X denotes oxygen or an NR⁶ group, in which R⁶ is hydrogen or represents an alkyl group having 1 to 4 C atoms, or in which R⁶ together with R⁵ and the nitrogen atom, forms a 5- to 7-membered heterocyclic ring, which is optionally substituted by a COO-alkyl group (1 to 4 C atoms) or by 1 or 2 alkyl groups (in each case 1 to 4 C atoms), and
R⁵ denotes a bulky hydrocarbon radical which occupies a large space and has up to 30 carbon atoms or a heteroaryl radical having 4 to 14 carbon atoms, which contains 1 heteroatom from the group consisting of nitrogen, oxygen and sulphur, where the hydrocarbon and heteroaryl radicals mentioned are optionally substituted by halogen, hydroxyl, alkyl and/or alkoxy having in each case 1 to 8 carbon atoms, with the proviso that when R⁵ is a tertiary butyl group or X represents the radical NR⁶, R¹ must be a methyl group,
and
R³ denotes hydrogen or, together with R⁴, denotes a tri- or tetramethylene group,
or in which
[C]
R¹ represents fluorine,
R² represents a radical of the formula (II) given under [B], wherein R⁴ represents a straight-chain or branched $C_1$–$C_8$-alkyl, a $C_7$–$C_{12}$-aralkyl, a $C_3$–$C_{10}$-cycloalkyl, a $C_6$–$C_{14}$-aryl or a furyl, thienyl or pyridyl radical, each of which is optionally substituted by benzyloxycarbonyl, alkoxycarbonyl having up to 6 C atoms, hydroxyl, alkyl, cycloalkyl or alkoxy having in each case up to 6 C atoms, halogen, phenoxy, benzoxy, acylamino having up to 8 C atoms or by carbonylalkoxy having up to 6 C atoms,
X denotes oxygen or an N⁶ group, in which
R⁶ represents hydrogen or straight-chain or branched $C_1$–$C_4$-alkyl or, together with R⁵ and the nitrogen atom, forms a 5- to 7-membered ring, which is optionally substituted by an alkoxycarbonyl group having up to 6 carbon atoms or by one or two alkyl groups each having 1 to 4 carbon atoms,
R⁵ represents a straight-chain or branched $C_1$–$C_{22}$-alkyl, $C_7$–$C_{12}$-aralkyl, $C_3$–$C_{10}$-cycloalkyl, $C_6$–$C_{14}$-aryl or a terpenyl radical, each of which is optionally substituted by halogen, alkyl or alkoxy having in each case 1 to 4 C atoms,
and
R³ represents hydrogen or $C_1$–$C_4$-alkyl or, together with R¹, forms a tri- or tetramethylene group,
or in which
[D]
R¹ represents hydrogen, methyl or fluorine,
R² represents a radical of the formula (II) given under [B], wherein
R⁴ represents a radical of the general formula (III)

—A—S(O)$_n$—R⁷, wherein n denotes the number 0,
R⁷ represents alkyl having up to 8 C atoms, phenyl or

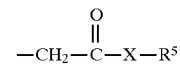

or, together with R³, forms a bridge described there and
A represents a methylene or a dimethylene group,
R⁵ represents a $C_{10}$-terpenyl radical, an adamantyl radical or a decahydronaphthyl radical, or represents an alkyl radical or cycloalkyl radical having in each case up to 12 C atoms, with the exception of methyl and ethyl, which is optionally mono- or disubstituted by $C_6$–$C_{10}$aryl, $C_1$–$C_4$-alkoxy, $C_3$–$C_{12}$-cycloalkyl or halogen, where the aryl and cycloalkyl radicals mentioned can in turn can again be substituted by $C_1$–$C_4$-alkyl,
X denotes oxygen or an NR⁶ group, in which R⁶ represents hydrogen or $C_1$–$C_4$-alkyl or, together with R⁵, forms a nitrogen-containing 5- to 7-membered ring, which can optionally be mono- or disubstituted by $C_1$–$C_4$-alkyl or $C_1$–$C_6$-alkoxycarbonyl,
and
R³ denotes hydrogen or methyl or, together with R⁷, forms a methylene group, which can be mono- or disubstituted by methyl or monosubstituted by tertiary butyl, or a dimethylene group,
or in which
[E]
R¹ represents hydrogen, methyl or fluorine,
R² represents a radical of the formula (II) given under [B], wherein
R⁴ represents the radical of the formula (III) given under [D], wherein n denotes the number 1 or 2, $R^7$ represents a straight-chain, branched or cyclic alkyl radical having up to 10 C atoms, $C_6$–$C_{14}$-aryl,

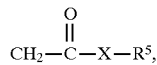

$C_2$–$C_{10}$acyl, optionally substituted benzoyl or benzyl or, together with $R^3$, forms a bridge described there and A represents a methylene or dimethylene group which is optionally mono- or disubstituted by $C_1$–$C_4$-alkyl, $R^5$ represents a straight-chain, branched or cyclic alkyl radical having up to 20 C atoms, which is optionally mono- to trisubstituted by halogen, alkoxy having 1 to 4 C atoms, aralkoxy having 7 to 16 C atoms or aryl having 6 to 10 C atoms, X has the meaning given above under [D], and $R^3$ represents hydrogen or $C_1$–$C_4$-alkyl or, together with $R^7$, forms a methylene group or a dimethylene group, which can be mono- or disubstituted by $C_1$–$C_4$-alkyl, or in which

[F]

$R^1$ represents hydrogen, methyl or fluorine, $R^2$ represents a radical of the formula (II) given under [B], wherein $R^4$ represents $C_1$–$C_5$-alkyl, $CH_2$-C-O-A, $CH_2$-S-A, ($CH_2$-S-$CH_3$, $CH_2$-cyclohexyl, cyclohexyl, phenyl, benzyl, 4A-O-benzyl, $CH_2$-benzyl, indolyl, $CH_2$-naphthyl or naphthyl, wherein A is hydrogen, methyl, t-butyl or benzyl, X represents —NH— and $R^5$ represents a radical of the general formula (IV)

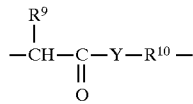

wherein $R^9$ can have the meanings given for $R^4$ and is identical to or different from this radical, Y represents oxygen or $NR^6$, wherein $R^6$ is hydrogen, methyl or ethyl or, together with $R^{10}$, forms a $C_5$–$C_6$-cycloalkyl radical and $R^{10}$ represents a straight-chain or branched $C_3$–$C_{18}$-alkyl radical or a $C_3$–$C_{12}$-cycloalkyl radical which is mono- to tetrasubstituted by $C_1$–$C_4$-alkyl, or benzyl or 1-phenylethyl, or represents phenyl which is mono- or disubstituted by fluorine, chlorine, trifluoromethyl, methoxy or $C_1$–$C_4$-alkyl and $R^3$ represents hydrogen.

4. Chiral polymers bonded to a support according to claim 3, wherein the monofunctional chiral vinyl monomers are optically active (meth)acrylamide monomers of the formula (I), wherein

[A]

$R^1$ represents hydrogen or methyl; and $R^2$ represents one of the stereoisomers of the eight possible stereoisomeric forms of the optically active radical of the formula:

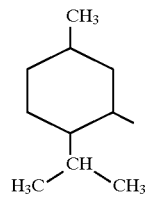

and $R^3$ represents hydrogen;

or wherein

[B], [C], [D], or [E]

the (meth)acrylamide monomers contain a single amino acid unit, wherein the amino acid is selected from the group consisting of alanine, aminobutyric acid, valine, norvaline, leucine, isoleucine, terleucine, phenylglycine, naphthylglycine, phenylalanine, thienylalanine, pyridylalanine, naphthylalanine, cyclohexylglycine, cyclohexylalanine, tyrosine, tryptophan, serine, aspartic acid, glutamic acid, ornithine, lysine, proline and 6-aminopenicillanic acid;

or a single amino acid unit, wherein the amino acid is selected from the group consisting of cysteine, homocysteine, penicillamine and methionine, wherein the SH function of each is optionally alkylated, arylated, alkoxycarbonylmethylated or bonded to the amino group thereof via an alkylene bridge, and/or the sulphur atom thereof is optionally oxidized to sulphoxide or sulphone;

or wherein

[F]

the (meth)acrylamide monomers contain a single dipeptide unit wherein both amino acids of said dipeptide unit are independently selected from the group consisting of alanine, aminobutyric acid, valine, norvaline, leucine, isoleucine, terleucine, norleucine, neopentylglycine, serine, cysteine, methionine, hexahydrophenylalanine, hexahydrophenylglycine, phenylglycine, phenylalanine, tyrosine, homophenylalanine, tryptophan, naphthylalanine and naphthylglycine.

5. Chiral polymers bonded to a support according to claim 1, characterized in that the polymer coating is 15 to 25% by weight, based on the total weight.

6. Chiral polymers bonded to a support according to claim 1, characterized in that the inorganic support material carries hydroxyl and/or amino groups on the surface.

7. Chiral polymers bonded to a support according to claim 1, characterized in that the inorganic support material is a silica gel.

8. Process for the preparation of chiral polymers bonded to a support according to claim 1, said process comprising coating inorganic support materials with mercapto groups (SH groups), subsequently reacting the mercapto group-coated inorganic support material with optically active monofunctional vinyl monomers, mixtures of various optically active monofunctional vinyl monomers or mixtures of optically active monofunctional vinyl monomers with vinyl monomers which are not optically active, said monomers optionally being bound to a spacer group, and polymerizing the monomers so that a chiral linear polymer results, which chiral linear polymer is coated on said inorganic support in an amount of 5 to 40% by weight based on the total weight.

9. In a process for the separation of optical isomers, the improvement which comprises using a chiral polymer bonded to a support according to claim 1 to effect the separation.

* * * * *